(12) United States Patent
Tackett et al.

(10) Patent No.: US 8,153,039 B2
(45) Date of Patent: Apr. 10, 2012

(54) METHOD FOR PRODUCING AND MONITORING THE COMPRESSIVE STRENGTH OF FOAM INSULATION BOARD

(75) Inventors: Timothy Tackett, Sheridan, IN (US); John B. Letts, Carmel, IN (US)

(73) Assignee: Firestone Building Products Co., LLC, Indianapolis, IN (US)

( * ) Notice: Subject to any disclaimer, the term of this patent is extended or adjusted under 35 U.S.C. 154(b) by 481 days.

(21) Appl. No.: 12/124,373

(22) Filed: May 21, 2008

(65) Prior Publication Data

US 2009/0048361 A1    Feb. 19, 2009

Related U.S. Application Data

(63) Continuation of application No. 10/925,654, filed on Aug. 25, 2004, now Pat. No. 7,387,753.

(60) Provisional application No. 60/497,675, filed on Aug. 25, 2003.

(51) Int. Cl.
*B29C 44/30* (2006.01)
*B29C 44/60* (2006.01)

(52) U.S. Cl. ....... 264/40.1; 264/45.8; 264/145; 264/161

(58) Field of Classification Search .................. None
See application file for complete search history.

(56) References Cited

U.S. PATENT DOCUMENTS

| | | | |
|---|---|---|---|
| 2,122,203 A * | 6/1938 | Gogan | 73/83 |
| 3,541,842 A * | 11/1970 | Clark et al. | 73/81 |
| 3,706,516 A | 12/1972 | Kisteneich et al. | |
| 3,786,676 A | 1/1974 | Korolyshun et al. | |
| 4,103,538 A * | 8/1978 | Stoferle et al. | 73/81 |
| 4,138,883 A | 2/1979 | Talbert | |
| 4,140,008 A * | 2/1979 | Golembeck et al. | 73/78 |
| 4,318,999 A | 3/1982 | Dunlop et al. | |
| 4,972,002 A | 11/1990 | Volkert | |
| 5,182,309 A | 1/1993 | Hützen | |
| 5,333,492 A * | 8/1994 | Aarts | 73/49.3 |
| 5,472,990 A | 12/1995 | Craig et al. | |
| 5,686,499 A | 11/1997 | Fishback | |
| 5,837,742 A | 11/1998 | Fishback | |
| 5,846,462 A | 12/1998 | Thompson | |
| RE36,674 E | 4/2000 | Gluck et al. | |
| 6,140,383 A | 10/2000 | Soukup et al. | |
| 6,427,524 B1 * | 8/2002 | Raspante et al. | 73/45.4 |
| 7,387,753 B2 | 6/2008 | Tackett et al. | |
| 2004/0082676 A1 | 4/2004 | Douglas et al. | |

FOREIGN PATENT DOCUMENTS

| | | | |
|---|---|---|---|
| DE | 19730891 | * | 2/1999 |
| EP | 0 404 086 A2 | | 12/1990 |
| EP | 0 825 438 A2 | | 2/1998 |
| WO | WO 00/24813 A1 | | 5/2000 |
| WO | WO 02/072680 A1 | | 9/2002 |

* cited by examiner

*Primary Examiner* — Edmund H. Lee

(74) *Attorney, Agent, or Firm* — Jason A. Houser; Arthur M. Reginelli

(57) ABSTRACT

A method for producing foam insulation board, the method comprising forming a foam product as part of a continuous process, where said foam product includes at least one side edge, monitoring on-line the compressive strength of the foam product, along said at least one side edge, and adjusting said step of forming a foam product in view of data obtained from said step of monitoring.

18 Claims, 6 Drawing Sheets

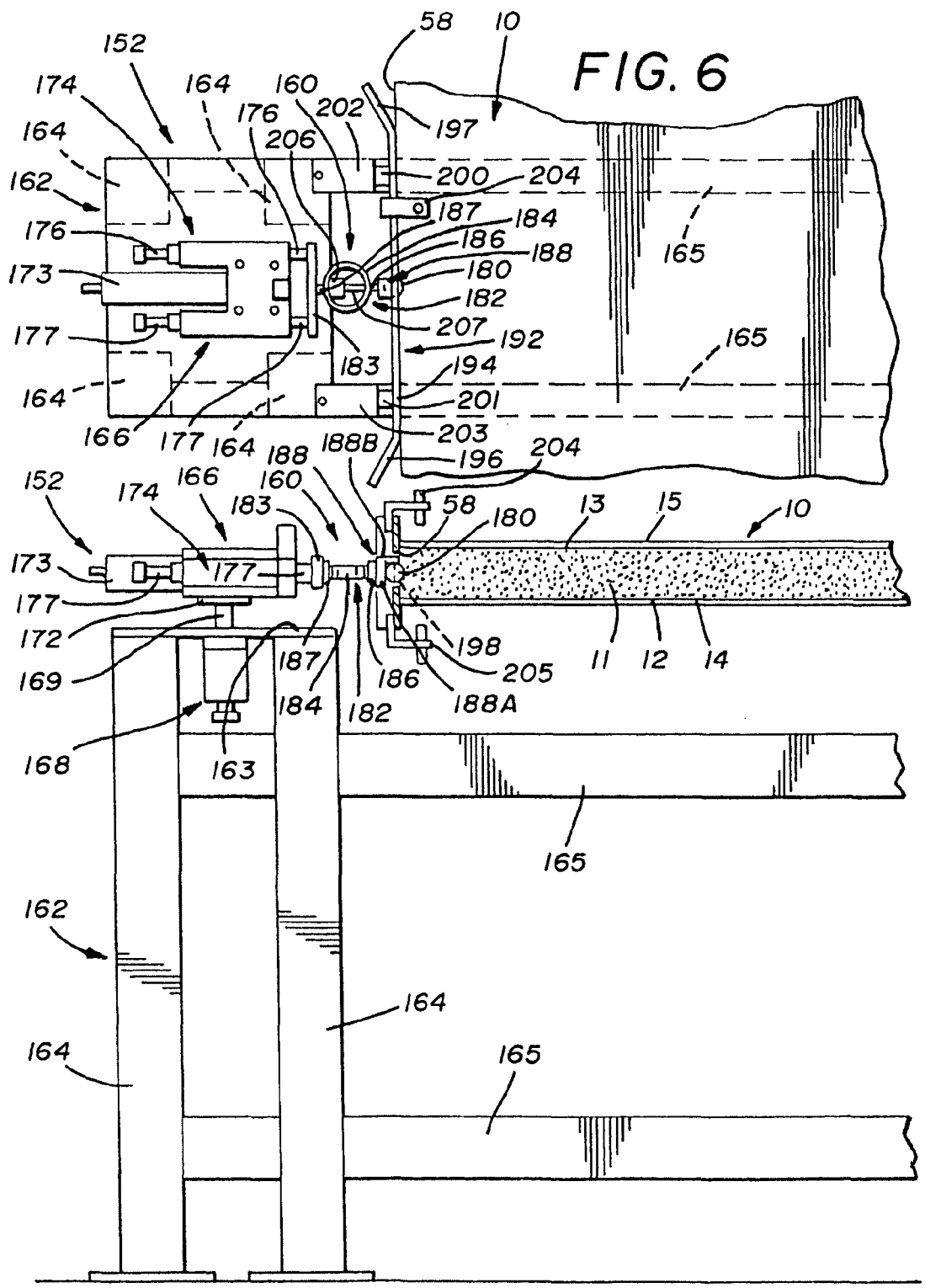

METHOD FOR PRODUCING AND MONITORING THE COMPRESSIVE STRENGTH OF FOAM INSULATION BOARD

This application is a continuation application of U.S. Non-Provisional application Ser. No. 10/925,654, filed in Aug. 25, 2004, now U.S. Pat. No. 7,387,753, which claims the benefit of U.S. Provisional Application No. 60/497,675, filed in Aug. 25, 2003, now abandoned, which Applications are incorporated herein by reference in their entirety.

FIELD OF THE INVENTION

This invention relates to a method and apparatus to monitor the compressive strength of insulation boards along their trimmed edges during manufacture of the boards.

BACKGROUND OF THE INVENTION

Polyurethane and polyisocyanurate foam insulation boards are commonly employed in the construction industry. These insulation boards are generally cellular in nature and typically include an insulating compound trapped within the cells of the foam.

The physical characteristics of the board are important to the overall performance of the board. For example, dimensional stability is important because insulation boards are exposed to a full range of weather. Where insulation boards are employed to insulate flat or low-slope roofs, shrinkage of these insulation boards from cold temperatures can cause a loss of insulating efficiency. In particular, when the dimensional stability of the foam matrix is low, the edges (especially the 8' edges of, for example, standard 4'×8' boards) are susceptible to edge collapse during exposure to cold temperatures. This collapse can cause the top facers and bottom facers along these edges to bend towards each other.

As a result, it is common in the industry to test insulation boards for cold-age dimensional stability (ASTM D2126). Alternatively, the dimensional stability of insulation boards, primarily the edges, can be determined by analyzing the perpendicular compressive strength of these edges (i.e. the compressive strength in the cross-machine direction). The higher the perpendicular compressive strength of the insulation boards along these edges, the better the cold age dimensional stability of the insulation boards.

The dimensional stability of insulation boards is believed to be impacted, especially near the edges of the board, by the degree of polyurethane crosslinking (isocyanurate formation). Incomplete crosslinking tends to be a problem near the edges of the board because less heat is present at the edges following manufacture of the boards. In other words, the boards are typically stacked or bundled following manufacture, and the heat that is generated and trapped within the boards tends to drive crosslinking; the exposed surface area around the edges of the stacks or bundles allows the edges to cool more rapidly which results in decreased crosslinking.

Also, the dimensional stability of insulation boards is believed to be impacted, especially near the edges of the board, by the shape and orientation of the cells within the foam. Particularly, it is believed that if the cells of the foam matrix are spherically-shaped, instead of being egg-shaped, then the dimensional stability of the roofing board is relatively high; but if the cells are egg-shaped, then the dimensional stability of the roofing board is relatively low along at least one of the three major axes. For example, if the major (as opposed to minor) axes of the egg-shaped cells are aligned parallel to the rise direction of the foam (i.e. perpendicular to the facers), then the dimensional stability perpendicular to the rise direction will be relatively low.

Several solutions have been suggested in the prior art and/or are practiced commercially to improve the dimensional stability of the insulation boards, particularly along edges. These solutions primarily involve adjusting manufacturing parameters. These parameters include, but are not limited to, manufacturing techniques, conditions, ingredients, and ingredient amounts. Thus, one could use compressive strength analysis to glean dimensional stability and alter these manufacturing parameters to produce an insulation board having a technologically useful dimensional stability.

But, the problem encountered derives from the fact that insulation boards are commercially produced in a continuous operation. These continuous manufacturing processes can suffer from quality control issues—particularly related to dimensional stability along the edges because adjustments to these processing parameters are best made during the process. Heretofore in the art, these adjustments to the processing parameters were made only after an insulation board was removed from the process, analyzed for compressive strength, and the data from this test was provided to an operator who could then make the appropriate adjustments. Not only is the removal of the board from the manufacturing process labor intensive, but depending upon the frequency of the quality control tests, hundreds of feet of insulation board could be manufactured before appropriate adjustments could be made to correct for quality control issues.

There is therefore a need to improve the manufacturing process of insulation boards such that quality control, particularly dimensional stability, can be improved.

SUMMARY OF THE INVENTION

The present invention provides a method for producing foam insulation board, the method comprising forming a foam product as part of a continuous process, where said foam product includes at least one side edge, monitoring on-line the compressive strength of the foam product, along said at least one side edge, and adjusting said step of forming a foam product in view of data obtained from said step of monitoring.

BRIEF DESCRIPTION OF THE DRAWINGS

FIG. 6 is a fragmentary plan view of another embodiment of an edge-strength-measuring device employed in the present invention.

FIG. 7 is a fragmentary elevational view from the rear of the edge-strength measuring device depicted in FIG. 6.

DETAILED DESCRIPTION OF ILLUSTRATIVE EMBODIMENTS

The present invention includes a process whereby insulation boards are manufactured and the compressive strength along the edges of the foam product is monitored on-line as part of the manufacturing process. In one preferred embodiment, the compressive strength is monitored continuously throughout the manufacturing process. By having continuous real-time compressive strength data, an operator can adjust the manufacturing process to ensure the proper quality of the insulation boards.

The insulation boards that are produced include those that are conventional in the art except for their improved quality or consistency as a result of the advantages offered by practicing the present invention. Preferred boards include those having a polyurethane or polyisocyanurate foam core. Polyurethane and polyisocyanurate foams are produced in a continuous manufacturing process by contacting an "isocyanate component" with a "polyol component." The "isocyanate component" generally includes an isocyanate or polyurethane prepolymer. "Polyol component" generally includes a polyol and/or glycol, and, usually, small amounts of water, but "polyol component" refers to any isocyanate-reactive component as generally known in the art, including, for example, noon-limiting example, diols, glycols, polyols, water, and primary and secondary amines. A blowing agent is typically dissolved in or emulsified in the polyol component. The isocyanate and polyol components are contacted and dispensed onto a moving form, where they react and produce heat. The evolving heat and the chemical reactions taking place serve, together with other factors such as frothing, generally cause formation of a cellular foam product. It is believed that the heat causes the blowing agents, such as pentanes, which are added as liquids, to volatize and form gas that becomes suspended in the reaction mixture to produce a cellular foam. Water, added purposefully or as part of the polyol component, reacts with isocyanate to produce carbon dioxide ($CO_2$), which is also suspended in the reaction mixture to produce a foam. The isocyanate component is typically delivered to the manufacturing process as part of an "A-side" stream of reagents and the polyol component is typically delivered as part of a "B-side" stream of reagents. Processes for the manufacture of polyurethane and polyisocyanurate foam insulation boards, as well as the ingredients and useful amounts thereof, are generally known in the art as described in U.S. Patent Application Publication No. 2004/0082676, which is incorporated herein by reference.

Figure 1:
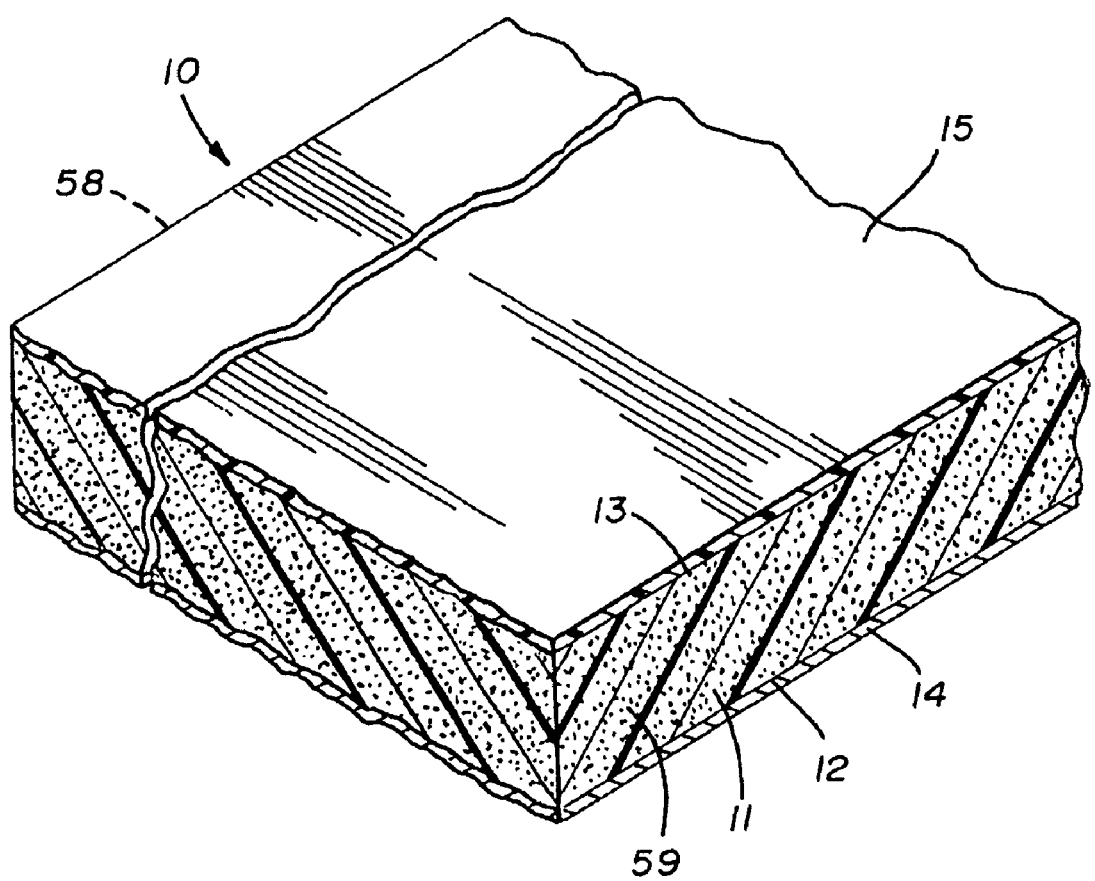
FIG. 1 is a fragmentary perspective cross-sectional view of an insulation board.

FIG. 1 shows a foam product 10, which includes a foam matrix 11 having a first major surface 12 and second major surface 13. An optional first facer material 14 and an optional second facer material 15 mate with first major surface 12 and second major surface 13, respectively. Foam product 10 includes first side edge 58 and second side edge 59. These edges continue along the entire length of foam product 10 (i.e., parallel to the longitudinal or machine direction of matrix 11) and are adjacent to the side plates of the laminator (not shown). These edges are perpendicular to the plane formed by facers 14 and 15, and may also be referred to as rise edges. Unless specifically distinguished herein, reference to edges refers to these side edges 58 and 59.

Foam product 10 preferably has a thickness from about 1 to about 4 inches, and during at least a portion of the production process, the length of the foam product is continuous so long as reactants are available to form the foam product. Although not specifically shown, foam product 10 is ultimately sized to desired dimensions depending on the intended application. For example, foam product 10 can be trimmed to a width of 4 feet and cut to length of 8 feet to form a 4'×8' insulation board, which size is often useful in the building trades.

Foam matrix 11 can be polyisocyanurate foam, polyurethane foam, or mixtures thereof. Foam matrix 11 is generally of standard production, and generally includes those having an index of about 250. Particularly, when polyisocyanurate foam is employed, those having an index above 200 are preferred; and when polyurethane foam is employed, an index above 120 is preferred. Nominal density of the polyisocyanurate or polyurethane foam is about 2 pounds per cubic foot (pcf).

First facer material 14 and second facer material 15 can comprise a polymer material, a reinforced polymer material, or a reinforced cellulosic material, as well as paper, aluminum foil and trilaminates thereof. The polymer material can include polypropylene, polymer latexes, polyamides, or mixtures thereof, and the cellulosic material can include recycled paper, cardboard, and the like.

Thicknesses of the facers typically range between about 0.01 and 0.15 inches. An exemplary polyamide facer material includes polyamide 6,6 although other polyamides are equally suitable. The thickness of a polyamide facer of the present invention ranges from about 0.25 mils to about 10 mils, preferably from about 0.4 mils to about 8 mils, and most preferably from about 0.5 mils to about 6 mils.

While practice of this invention does not generally alter the conventional methods that are used to continuously produce insulation boards, it is believed that the invention is best described by describing the overall manufacturing process. A typical continuous process for the manufacture of insulation boards is depicted in FIGS. 2 and 3 in conjunction with a first apparatus portion 20 (FIG. 2) and a second apparatus portion 50 (FIG. 3).

Figure 2:
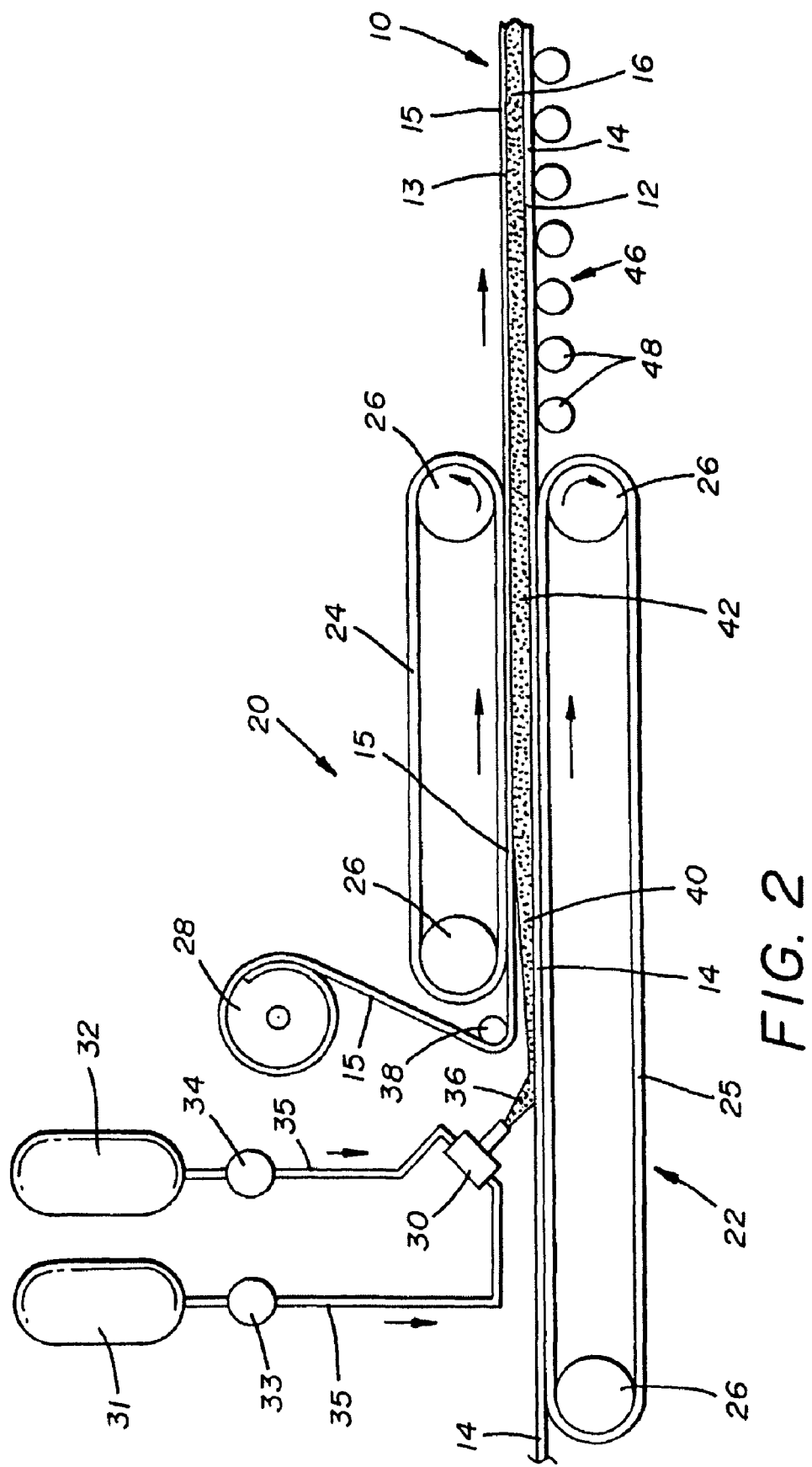
FIG. 2 is a side elevational view of a preferred apparatus for the continuous production of the insulation board.
Figure 3:
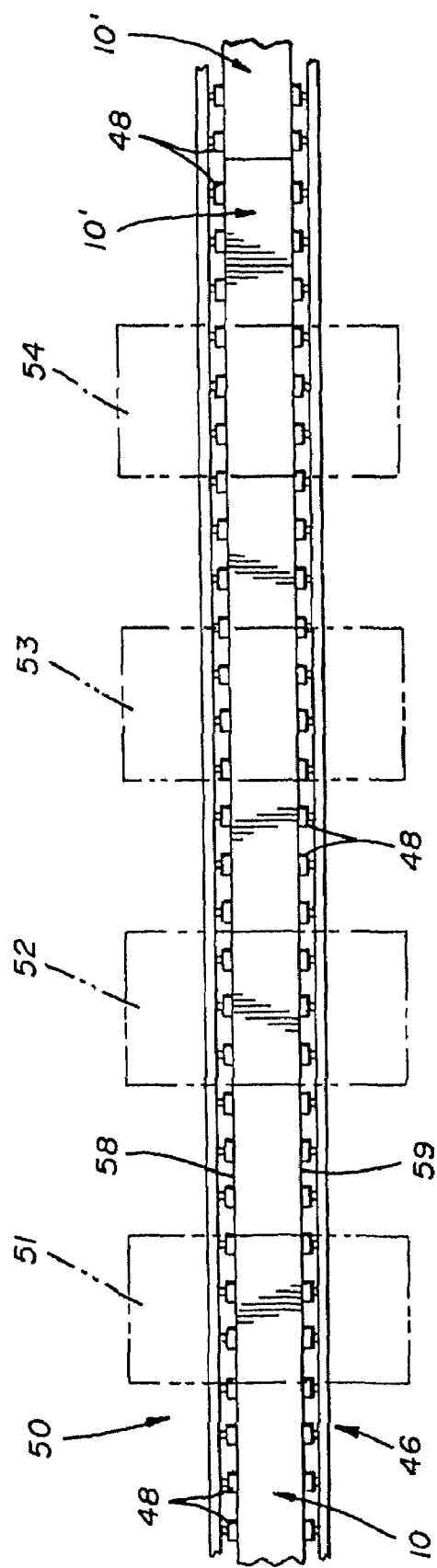
FIG. 3 is a fragmentary schematic view of the second half of the manufacturing apparatus used to produce the insulation board.

As shown in FIG. 2, the first apparatus portion 20 includes a laminator assembly 22. Laminator assembly 22 includes a continuous upper belt 24 and a continuous lower belt 25, which are both reeved around a series of rollers 26. Several of the rollers 26 are preferably driven and provide for the movement of first facer material 14 and second facer material 15. For example, second facer material 15 is initially carried by a spool 28, and is thereafter fed into position in laminator assembly 22 by continuous upper belt 24.

A foam mixhead 30 is positioned immediately above first facer material 14 as it enters laminator assembly 22. Foam ingredients (i.e., the A-side and B-side reagents) are delivered from reservoirs 31 and 32, fed through metering pumps 33 and 34, and through appropriate conduits 35 into a mixhead 30, where upon contact with one another, a reaction commences to form foam matrix 11.

Mixhead 30 supplies an appropriate mixture 36 of foam ingredients from the reservoirs 31 and 32, as well as an appropriately metered amount thereof, onto the surface of first facer material 14. Subsequently, and slightly downstream of foam mixhead 30, second facer material 15 is fed into laminator assembly 22 from spool 28. Before contacting mixture 36, second facer material 15 passes around a feed roller 38 that positions second facer material 15 against upper belt 24. As lower facer material 14, upper facer material 15, and mixture 36 are conveyed, mixture 36 rises, as depicted at 40, until second facer 15 is in complete contact with upper belt 24. Upper belt 24 and lower belt 25 are adjustable to accommodate the desired thicknesses of matrix 11.

After the foaming of mixture 36 has completed, an intermediate foam product 42 (FIG. 2) may be heated to effect curing. For example, intermediate foam product 42 can be passed through ovens or heaters (not shown). After curing for the appropriate time and temperature, continuous foam product 10 emerges from first apparatus portion 20 and is directed toward second apparatus portion 50 by a conveyer 46.

As discussed above, the advantageous monitoring of the present invention preferably occurs once foam product 10 passes through first apparatus portion 20. On-line monitoring of the compressive strength refers to the fact that the compressive strength is measured without removing the continuous product 10 (or the resultant insulation boards 10' shown in FIG. 3) from the production line during the manufacturing process. Indeed, monitoring occurs while the continuous product 10 or insulation boards 10' travel along the conveyer 46 during the manufacturing process. While the monitoring of the compressive strength is preferably continuous, which refers to the fact that the monitoring persists through the manufacturing process, the monitoring can be performed intermittently or in intervals as the manufacturing process warrants. For example, monitoring can occur at every other 8' length of matrix 11 or foam product 10, or monitoring can occur at intervals, for example an 8' length within a larger segment of foam product 10, such as a 100' length.

A preferred apparatus for conducting on-line monitoring is described with reference to FIG. 3. For example, as seen in FIG. 3, second apparatus portion 50 includes a trimming implement 51, an edge-strength measuring device 52, an optional perforation implement 53, and a sawing implement 54. Foam product 10 is directed through second apparatus portion 50 by conveyer 46 having rollers generally indicated by the numeral 48 in FIGS. 2 and 3. Foam product 10 emerges from second apparatus portion 50 as insulation board 10'. The position within second apparatus portion 50 at which the on-line monitoring occurs is not critical. In fact, on-line monitoring may take place before or after the trimming step, before or after the optional perforation step, or before or after the cutting step. With this understanding, further reference to on-line monitoring will be made with respect to foam matrix 11, which may be included in either continuous product 10 or board 10'.

Trimming implement 51 is used in a trimming operation to trim to size continuous product 10 or board 10' in the direction that conveyer 46 is moving (i.e. the so-called machine direction). That is, trimming implement 51 is provided to trim the edges of continuous product 10 or board 10' aligned in the machine direction to provide trimmed edges trimmed edges 58 and 59, which are shown in FIG. 1, and which are preferably parallel to one another. The distance between the trimmed edges 58 and 59 provides the width of boards 10'. For example, if boards 10' are sized to be 4'×8', the distance between trimmed edges 58 and 59 would likely be 4'.

Although edge-strength measuring device 52 can be positioned before or after the trimming implement 51, the trimming operation is preferably performed before foam product 10 or board 10' enters edge-strength measuring device 52. Advantageously, when edge-strength measuring device 52 interfaces with flat or trimmed edges, edge-strength measuring device 52 provides relatively more consistent measurements. Accordingly, trimmed edges 58 and 59 are preferably formed (via trimming) on the continuous product 10 or board 10' before the compressive strength of the foam matrix 11 is measured.

Perforation implement 53 is preferably used to provide proper lamination of first facer material 14 and second facer material 15 to foam matrix 11, and to facilitate application of hot asphalt to the insulated roofing boards by releasing unwanted gases such as moisture vapor generated during the manufacturing process or other gases associated with first facer material 14 and second facer material 15. Perforation implement 53 preferably includes a plurality of needles (not shown) arranged on either side of board 10'. The needles are used to perforate first facer material 14 and second facer material 15 to release pockets of unwanted gases, and to simultaneously drive portions of first facer material 14 and second facer material 15 into foam matrix 11. As such, the portions of first facer material 14 and second facer material 15 driven into foam matrix 11 are effectively interlocked with foam matrix 11.

Sawing implement 54 is used to cut continuous foam product 10 into boards 10' of desired length. As such, product 10 is cut in a direction perpendicular to the machine direction to provide foam boards 10'. Preferably, the step of sawing occurs after the step of trimming.

In a preferred embodiment, the compressive strength of the matrix 11 along trimmed edges 58 and 59 is continuously measured by employing the edge-strength measuring device 52. The preferred apparatus produces a signal representing the force imparted on the apparatus when engaged with trimmed edges 58 and 59. The signal is preferably calibrated to account for the area of contact between a contacting implement of edge-strength measuring device 52 and trimmed edges 58 and 59 to produce a pressure measurement. This pressure measurement can be related or translated to the compressive strength of foam matrix 11 along trimmed edges 58 and 59 thereof, and can be used by an operator to adjust the manufacturing process to provide necessary compressive strength according to specified tolerances.

Figure 4:
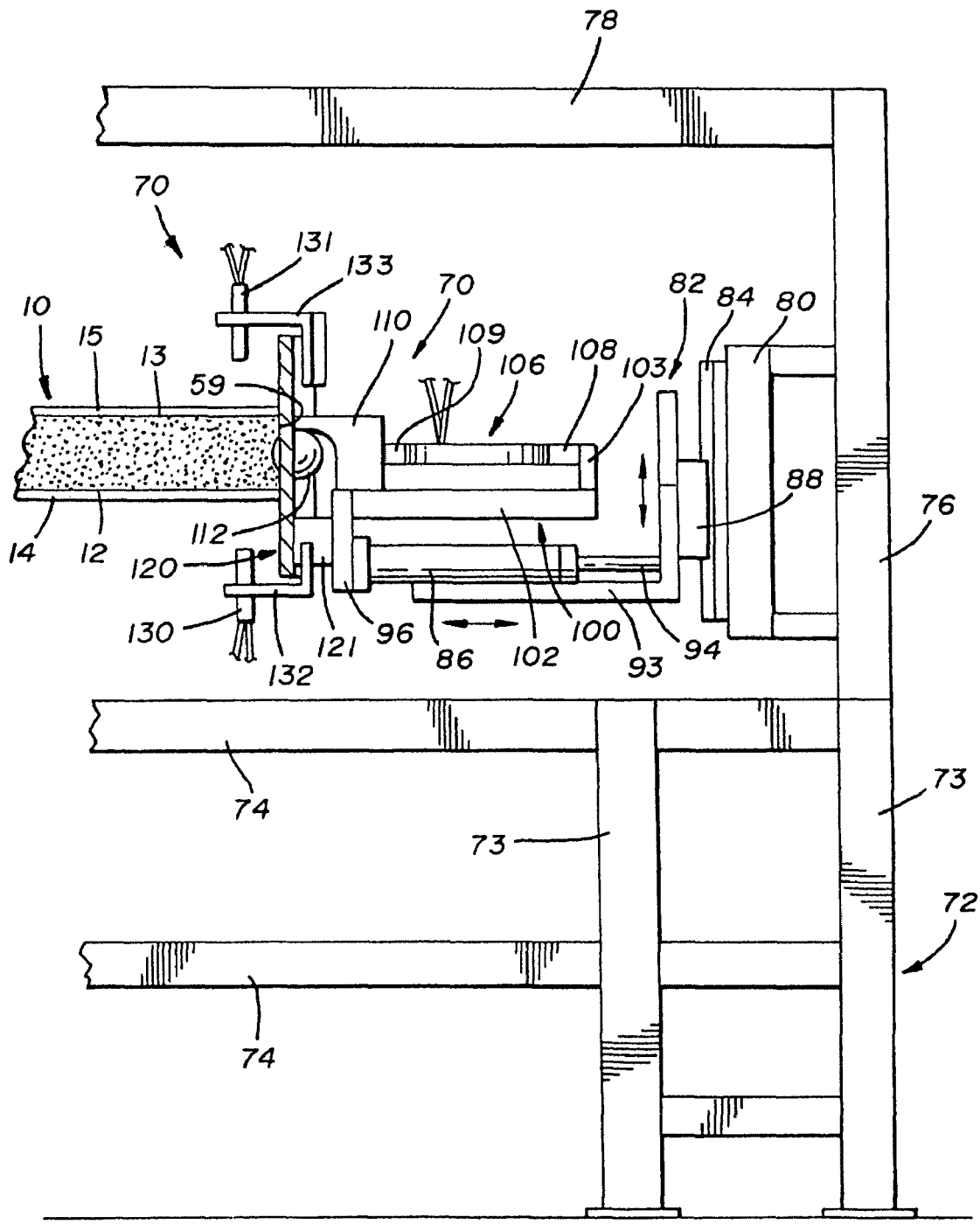
FIG. 4 is a fragmentary elevational view from the rear of one embodiment of an edge-strength measuring device employed in the present invention.
Figure 5:
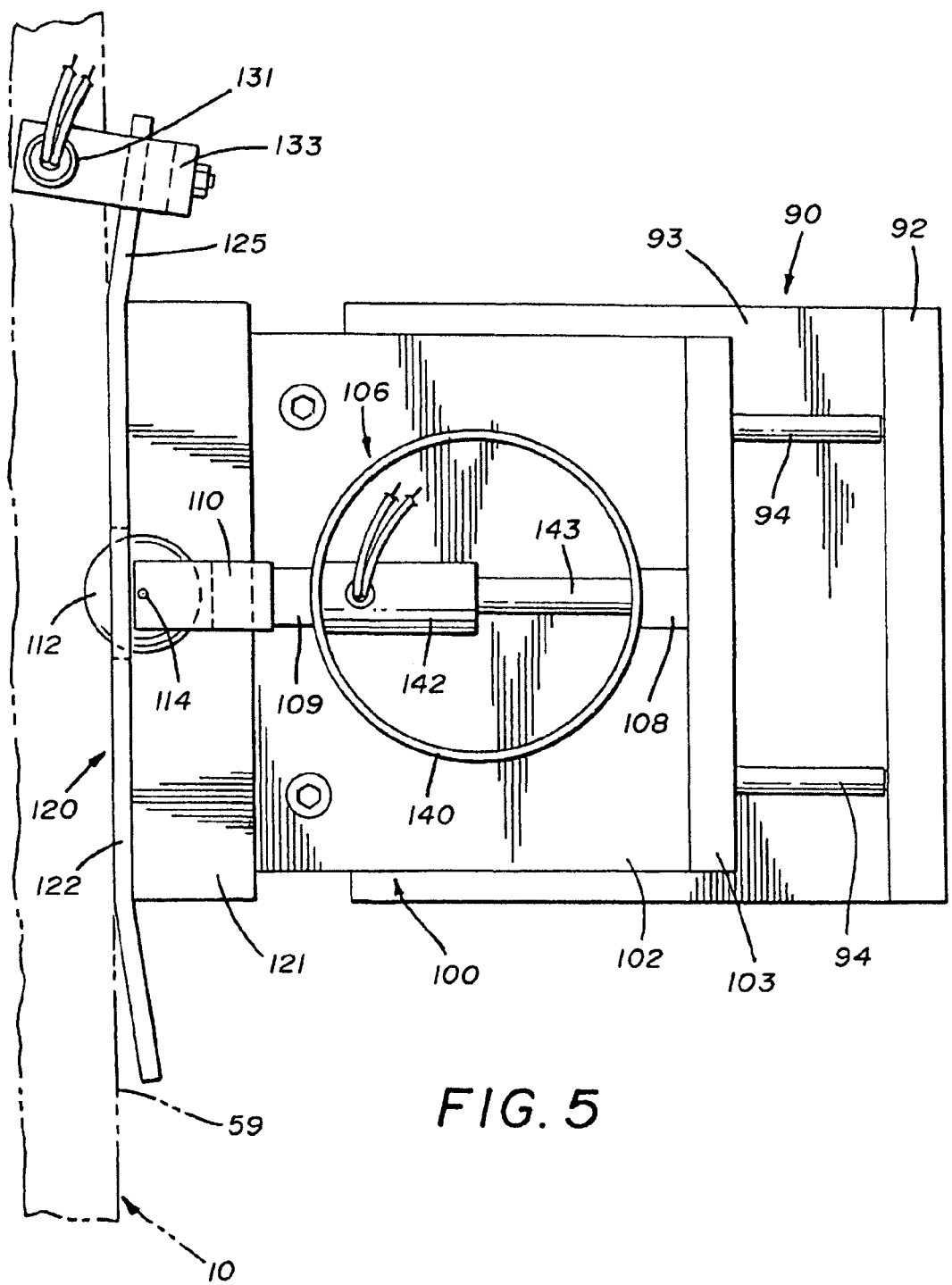
FIG. 5 is a fragmentary enlarged plan view of a measuring implement employed in the edge-strength measuring device depicted in FIG. 5.

The edge-strength measuring device 52 is shown in FIGS. 4 and 5. Edge-strength measuring device 52 includes two portions positioned adjacent the sides of the conveyer 46. Each of these two portions employ a measuring implement 70 positioned proximate to matrix 11 and oriented in the cross-machine direction to interface or engage with one of trimmed edges 58 and 59. Measuring implements 70 are likewise preferably positioned in opposed relation to one another. Preferably, the opposed measuring implements 70 are mirror images of one another and are aligned in the cross-machine direction on opposite sides of the continuous product 10 or boards 10'. For illustrative purposes, only half of edge-strength measuring device 52, including one of the opposed measuring implements, is shown in FIGS. 4 and 5.

Measuring implement 70 depicted in FIGS. 4 and 5 is disposed proximate the trimmed edge 59, and is supported by a stationary table 72 having legs 73 and braces 74 extending between the legs 73. A support post 76 extends upwardly from the stationary table 72 to support an upper brace 78 and an extension bracket 80. Extension bracket 80 supports a self-adjusting assembly 82. Braces 74 and upper brace 78 extend between the two opposed portions of the edge-strength measuring device 52 to provide a rigid interconnection therebetween.

Self-adjusting assembly 82 provides for the positioning of measuring implement 70, and includes a vertically-oriented linear slide 84 and a horizontally-oriented linear slide 86. Vertically-oriented linear slide 84 is attached to extension bracket 80 and includes a sliding member 88. Sliding member 88 is capable of moving vertically up and down, and connects the remainder of self-adjusting assembly 82 with extension bracket 80. As such, vertically-oriented linear slide 84 is capable of vertically repositioning measuring implement 70, and the remainder of self-adjusting assembly 82 (including horizontally-oriented linear slide 86).

As shown in FIG. 4, an L-shaped shelf 90 is attached to the sliding member 88 to connect horizontally-oriented linear slide 86 with sliding member 88. More specifically, L-shaped shelf 90 includes a first vertical member 92 attached to sliding member 88, and a second horizontal member 93. Second horizontal member 93 supports horizontally-oriented linear slide 86, which is capable of moving in and out relative to first vertical member 92. For example, horizontally-oriented linear slide 86 is capable of sliding on horizontal slide members 94 (both of which are shown in FIG. 5). Horizontal slide members 94 are parallel to one another, and serve as tracks for guiding horizontally-oriented linear slide 86. Horizontally-oriented linear slide 86, which is guided by horizontal slide members 94, is therefore capable of horizontally repositioning (in the cross-machine direction) measuring implement 70.

Positioning sensors such as photo-electric and ultrasonic sensors are preferably used to properly position the measuring implements 70 relative to trimmed edges 58 and 59. For example, first and second photo-electric cells 130 and 131 produce signals relating to the position of the matrix 11; these signals are preferably relayed to a computer microprocessor (not shown), which is attached to vertically-oriented linear slide 84 and horizontally-oriented linear slide 86. The computer microprocessor is capable actuating vertically-oriented linear slide 84 and horizontally-oriented linear slide 86 according to the signal to position measuring implements 70 so that they contact trimmed edges 58 and 59.

Self-adjusting assembly 82 also includes a vertically extending attachment plate 96 attached to horizontally-oriented linear slide 86 to support measuring implement 70 relative to horizontally-oriented linear slide 86. Attachment plate 96 supports an L-shaped supporting member 100 that includes a horizontal portion 102 and a vertical portion 103. As shown in FIGS. 4 and 5, horizontal portion 102 extends outwardly from attachment plate 96 over horizontally-oriented linear slide 86 and measuring implement 70 is attached to the vertical portion 103.

Measuring implement 70 includes a proving ring 106 having integrally attached first and second bosses 108 and 109. As shown in FIGS. 4 and 5, first boss 108 is attached to vertical portion 103 of the L-shaped supporting member 100, and second boss 109 is attached to a contoured bracket 110. Contoured bracket 110 is also part of measuring implement 70 and supports a contacting element 112 (i.e. a sphere, ball, cylinder, or the like), which is used to contact the matrix 11 of board 10. For example, as shown in FIGS. 4 and 5, the contacting element 112 is a sphere. The sphere employed as the contacting element 112 is attached to the contoured bracket 110 by a pin 114, and is able to rotate about the axis of the pin using various bearings (not shown).

When the measuring implements are properly positioned proximate to trimmed edges 58 and 59, contacting elements 112 interface with trimmed edges 58 and 59. To that end, the sphere, ball, cylinder, or the like are preferably made of materials that have limited adhesion with (and hence generate little friction when contacting) foam matrix 11 as the continuous product 10' or boards 10 are passing through device 52. For example, the sphere, ball, cylinder, or the like can be composed of a plastic material such as PVC or polyurethane, or can be composed of a metallic material such aluminum coated with a low-friction coating such as a fluoro-coating like Teflon™.

Contacting element 112 extends partially through an aperture (not shown) of a sled 120. Sled 120 is attached to attachment plate 96 (and the self-adjusting assembly 82) via a sled support post 121. Sled 120 is used to position contacting element 112 relative to foam matrix 11. For example, because continuous product 10 or boards 10' travel in the machine direction (from the bottom to the top of FIG. 5), sled 120 includes a non-slanted portion 122 (through which the above-discussed aperture is provided), a slanted portion 124, and optionally a second slanted portion 125. During operation of edge-strength measuring device 52, slanted portion 124 is used to funnel matrix 11 into position along non-slanted portion 122. When the matrix 11 is properly positioned relative non-slanted portion 122, contacting element 112, which extends partially through the aperture, contacts trimmed edge 59 (FIG. 4). Therefore, as trimmed edge 59 passes along sled 120, slanted portion 124 ensures proper positioning of matrix 11 with respect to non-slanted portion 122 and sphere 112.

With reference to FIG. 4, sled 120 is also preferably provided with first and second photo-electric cells 130 and 131, which serve as the above-discussed position sensors. First and second photo-electric cells 130 and 131 are respectively positioned using first and second brackets 132 and 133, which are opposed to one another proximate one end of sled 120. As such, as matrix 11 of continuous product 10 or boards 10' pass through device 52, matrix 11 passes between first and second photo-electric cells 130 and 131.

First and second photo-electric cells 130 and 131 are provided to measure the position of matrix 11 relative to contacting element 112. To that end, first and second photo-electric cells 130 and 131 provide signals proportional to the distance between themselves and, when appropriate, first major surface 12 or first facer material 14 and second major surface 13 or second facer material 15. A computer microprocessor can process these signals to determine whether measuring implements 70 are properly positioned relative to matrix 11. Other sensing devices can be employed such as ultrasonic sensors. As those skilled in the art appreciate, the use ultrasonic sensors obviate the need for sensing devices above and below matrix 11. Also, the process of this invention can be operated without sensing devices provide that the width of matrix 11 is known and provided that the position of matrix is fixed with respect to the conveyor 46.

Depending on the signals received from first and second photo-electric cells 130 and 131, a computer microprocessor can control the actuation of vertically-oriented linear slide 84 and horizontally-oriented linear slide 86 to position contacting element 112 such that it contacts foam matrix 11. In doing so, the computer microprocessor actuates vertically-oriented linear slide 84 and horizontally-oriented linear slide 86 to position contacting element 112 in the vertical center of the trimmed edge 59. First and second photo-electronic cells 130 and 131, and the control provided by the computer microprocessor, are used to maintain the proper position of contacting elements 112 relative to trimmed edges 58 and 59.

When contacting element 112 is properly positioned with respect to trimmed edge 59, for example, contacting element 112 presses into foam matrix 11 along trimmed edge 59, and foam matrix 11 resultantly exerts a force against the element 112. The positioning of contacting element 112 is preferably fixed with respect to sled 120. As a result, sled 120 is effectively pressed against trimmed edge 59 and contacting element 112 is positioned such that, as it is pressed into foam matrix 11, it is maintained at a constant depth. Preferably, the area of the impression is constantly maintained by the proper positioning of the measuring implement 70 (especially contacting element 112 and sled 120) by the computer microprocessor. Consequently, the outline of the impression or "footprint" of contacting element 112 will be constant as matrix 11 passes along conveyer 46 past measuring implement 70.

Proving ring 106 is adapted to measure the force exerted by foam matrix 11 on contacting element 112 and generate a signal that can be forwarded to the computer microprocessor. For example, the force exerted by foam matrix 11 is imparted through contacting element 112, contoured bracket 110, and second boss 109 to ring portion 140 of proving ring 106. Because proving ring 106 is exposed to the imparted force, ring portion 140 deforms in relation to the imparted force. That is, proving ring 106 is adapted to deform according to force imparted by foam matrix 11 on contacting element 112.

Ring portion 140 is preferably provided with a "linear variable differential transducer" (LVDT) 142 and an armature 143 to accurately measure the amount of imparted force. Armature 143 interacts with LVDT 142 to generate a signal proportional to the deformation of ring portion 140 and, hence, the imparted force. LVDT 142 and armature 143 are affixed on the interior of ring portion 140. For example, as seen in FIG. 5, armature 143 is affixed adjacent first boss 108, and LVDT 142 is affixed adjacent to second boss 109.

LVDT 142 includes a cylinder (or tube) and armature 143 is adapted to partially fit inside LVDT 142. A voltage is induced in LVDT 142, which varies according to the displacement of the armature 143 relative to LVDT 142, in order to generate a signal proportional to the imparted force. For example, armature 143 is preferably configured to be capable of moving 0.03" relative to LVDT 142, and using the induced voltage, LVDT 142 generates a signal that is linearly proportional to displacement (from 0.00 to 0.03") of armature 143 inside LVDT 142. Therefore, when ring portion 140 is deformed, armature 143 is displaced inside LVDT 142, and an appropriate signal is generated. Because there is a direct relationship between the imparted force, the deformation of ring portion 140, and the displacement of armature 143 inside LVDT 142, this signal is directly related to the magnitude of the imparted force.

The signal generated by LVDT 142 is relayed to the computer microprocessor, which modifies the signal according to the area of the footprint of contacting element 112 (as described hereinabove). The computer microprocessor is calibrated according to the area of the footprint to generate a pressure measurement indicating the compressive strength along, for example, trimmed edge 59. That is, the computer microprocessor converts the signals generated by LVDT 142 into quality control information (i.e., the pressure measurement) indicating the compressive strength along the edges of the foam matrix.

A second embodiment of the edge-strength measuring device is generally indicated by the numeral 152 in FIGS. 6 and 7, and, like the first embodiment (edge-strength measuring device 52), includes two portions positioned adjacent the sides of conveyer 48. Each of these two portions include a measuring implement 160 positioned proximate to matrix 11 to interface with trimmed edges 58 and 59 thereof. Like the two portions of edge-strength measuring device 52, the measuring implements 160 of edge-strength measuring device 152 are also positioned in opposed relation to one another aligned in the cross-machine direction on opposite sides of matrix 11. That is, the measuring implements 160 are mirror images of one another, and, consequently, for illustrative purposes, only half of edge-strength measuring device 152 including one measuring implement 160 is shown in FIGS. 6 and 7.

Measuring implement 160 depicted in FIGS. 6 and 7 is disposed proximate trimmed edge 58 on the left of conveyer 46 in the machine direction. To support measuring implement 160, edge-strength measuring device 152 includes a stationary table 162 including a support plate 163 and legs 164 extending downwardly from support plate 163. Braces 165 attached to legs 164 extend between the two portions of the edge-strength measuring device 152 underneath conveyer 46 to provide a rigid connection therebetween.

A self-adjusting assembly 166 is attached to support plate 163, and includes vertically-oriented linear slide 168, a vertical slide member 169 actuated by vertically-oriented linear slide 168, a platform bracket 172, a rail member 173, a horizontally-oriented linear slide 174 slidable on rail member 173, and first and second horizontal slide members 176 and 177.

As shown in FIG. 7, vertically-oriented linear slide 168 extends downwardly from support plate 163, and is positioned between legs 164. Vertical slide member 169 extends upwardly from vertically oriented linear slide 68 through an aperture (not shown) in support plate 163. Vertical slide member 169 is capable of vertical movement up and down via actuation of vertically-oriented linear slide 168.

Platform bracket 172 is attached to upper extremity of vertical slide 172, and supports of rail member 173. Horizontally-oriented linear slide 174 is slidable on rail member 173 in a direction perpendicular to the movement of continuous product 10' or board 10 on conveyer 46. As such, horizontally-oriented linear slide 174 can be roughly adjusted relative trimmed edge 58, and, as discussed below, first and second horizontal slide members 176 and 177 can be finely adjusted relative trimmed edge 58 to position measuring implement 160 proximate in proximity thereto.

First and second horizontal slide members 176 and 177 are positioned on opposite sides of horizontally-oriented linear slide 174, and are capable of reciprocal motion in the cross-machine direction. That is, first and second horizontal slide members 176 and 176 are capable of horizontal movement in and out relative trimmed edge 58 via actuation of horizontally-oriented linear slide 174. As such, the proper position of a contacting element 180 (i.e. a sphere, ball, cylinder, or the like used in the measuring implement 160) relative trimmed edge 58 is maintained by adjusting vertically-oriented linear slide 168 and horizontally oriented linear slide 174.

Measuring implement 160 includes a proving ring 182 is attached to an equalization arm 183 that extends between and is attached to the distal ends of first and second horizontal slide members 176 and 177. As seen in FIG. 6, proving ring 182 includes a ring portion 184 and first and second bosses 186 and 187 integrally formed with ring portion 184. First and second bosses 186 and 187 extend outwardly from opposite sides of ring portion 184. First boss 186 is attached along the center of the equalization arm 183, and second boss 187 is attached to an L-shaped bracket 188 supporting contacting element 180.

As shown in FIG. 6, L-shaped bracket 188 preferably includes first and second members 188A and 188B. Second boss 187 is attached to first member 188A, and the contacting element 180 (i.e. a sphere, ball, cylinder) is attached to second member 188B using a pin (not shown). Contacting element 180 can be provided with bearings such that it is capable of rotation relative to the pin.

With reference again to FIGS. 6 and 7, a sled 192 is attached to support plate 163 to ensure proper positioning of the continuous product 10' or boards 10. To that end, because matrix 11 travels in the machine direction (from the bottom to the top of FIG. 6), sled 192 includes a non-slanted portion 194, a slanted portion 196, and an optionally slanted portion 197. A vertically-oriented slot 198 is provided through non-slanted portion 194 for receiving a portion of contacting element 180. During operation, slanted portion 196 funnels continuous product 10' or board 10 in position along non-slanted portion 194.

Sled 192 is attached to stationary table 162 via first and second support brackets 200 and 201 which are respectively attached to first and second air cylinders 202 and 203. First and second air cylinders 202 and 203 are capable of reciprocally moving first and second brackets 202 and 203 to properly position sled 192 relative to matrix 11 or contacting element 180. Air cylinders 202 and 203 can be attached to or be configured to move in unison with horizontally-oriented slide 174 so as to maintain a constant position, in the cross-machine direction, of the contacting element 180 relative to sled 192. Otherwise, position sensors, in addition to those described below, may be required to maintain the degree to which contacting element 180 (i.e. sphere, ball, cylinder, or the like) is pressed into foam matrix 11.

Sled 192 can be provided with first and second photoelectric cells 204 and 205 to determine the position of matrix 11 relative to contacting element 180. First and second photoelectric cells 204 and 205 can be respectively positioned along the top edge of non-slanted portion 194, and are interconnected with a computer microprocessor or electronic processor (not shown). According to the signals received from first and second electric cells 204 and 205, the computer microprocessor (which is also connected to the self-adjusting assembly 166) alters the position of contacting element 180 relative the trimmed edge 58 by actuating vertically-oriented linear slide 168 and horizontally-oriented linear slide 174. For example, actuation of vertically-oriented linear slide 168 effects the position of contacting element 180 along vertically-oriented slot 198 and trimmed edge 58, and actuation of horizontally-oriented linear slide 174 effects the position of the contacting element 180 in the cross-machine direction relative to trimmed edge 58.

Ideally, the computer microprocessor controls actuation of self-adjusting assembly 166 to position the contacting element 180 in the vertical center of trimmed edge 58. When contacting element 180 is properly positioned relative to trimmed edge 58, contacting element 180 creates an impression in foam matrix 11. In doing so, foam matrix 11 resultantly exerts a force against contacting element 180. The footprint or area of the impression is constantly maintained by the proper positioning of contacting element 180 (i.e. sphere, ball, cylinder, or the like) and sled 92.

Operation of proving ring 182 is afforded by the rigid attachment of first boss 186 to the equalization arm, and of second boss 187 to L-shaped bracket 188 (which supports contacting element 180). For example, the force exerted by foam matrix 11 on contacting element 180 is imparted through L-shaped bracket 188, and second boss 187 to the ring portion 184 of proving ring 182. Ring portion 184 deforms according to the magnitude of the imparted force. To accurately measure the amount of the imparted force, ring portion 184, as seen in FIG. 6, includes an LVDT 206 and an armature 207.

LVDT 206 is a cylinder (or tube) affixed on the interior of proving ring 182 adjacent second boss 187. Armature 207 is adapted to partially fit within LVDT 206, and is affixed to the interior of proving ring 182 adjacent first boss 186. To generate a signal proportion to the imparted force, a voltage is induced in LVDT 206, and the magnitude of the induced voltage varies depending on the displacement of armature 207 inside LVDT 206. For example, armature 207 can be configured to be capable of moving 0.03" relative to LVDT 206, and using the induced voltage, LVDT 206 generates a signal that is linearly proportional to the displacement (from 0.00 to 0.03") of armature 207 inside LVDT 206. Therefore, when proving ring 182 is deformed, armature 207 is displaced inside LVDT 206, and an appropriate signal is generated.

As discussed in accordance with edge-strength measuring device 52, the signal generated by LVDT 206 of edge-strength measuring device 152 is relayed to the computer microprocessor which modifies the signal according to the area of the footprint of contacting element 180 to generate a pressure measurement indicating the compressive strength along trimmed edge 58, for example. The compressive strength measurement can be used as quality control information to allow an operator to continuously monitor the manufacturing run to effect the compressive strength along the edges of foam matrix 11 to ensure that boards 10' are sufficiently durable as to be resistant to edge collapse.

The quality control information allows an operator to continuously monitor the manufacturing run to effect the desired compressive strength along the edges of the foam matrix. The signals generated by LVDT 142 provide a feedback loop that allows the operator to adjust components of the manufacturing process to effect the desired compressive strength along the edges of the foam matrix and, thereafter, monitor whether the compressive strength has actually been modified. Consequently, the operator can continuously monitor and update the manufacturing process during a manufacturing run to ensure that foam matrix 11 of the board 10' is sufficiently resistant to edge collapse.

As noted above, the process of on-line monitoring provided by the present invention allows operators of the continuous foam making process real time information. With this information, the operator can make adjustments to the process that can improve the dimensional stability of the insulation boards, especially along the edges. There are numerous adjustments that an operator can make. For example, the level or amount of catalyst employed or added to the process as an ingredient can be adjusted. Typically the level of catalyst is proportional to the degree of cure. Also, the operator can alter the level or amount of the other ingredients employed to form the foam. For example, the type amount of blowing agent can be adjusted. Still further, the operator can alter the positioning of the mix heads above the conveyer. As those skilled in the art will appreciate, continuous processes for the manufacture of polyurethane or polyisocyanurate foam insulation boards employ multiple mix heads (e.g., three mix heads) that deposit the foam forming material onto the conveyer. The positioning of the outermost mix heads (i.e., those proximate to the side rails) can alter the formation of the foam, especially near the side rails, which can ultimately have an impact on dimensional stability. Even further, the operator can adjust the temperature of the heaters or ovens that may be employed to cure the foam. Once provided with real-time information as to the compressive strength along the edges of the board, operators will be able to develop several techniques or combinations thereof to adjust the process and thereby improve the dimensional stability (or the consistency of the dimensional stability throughout the manufacturing process) of the resultant boards.

Various modifications and alterations that do not depart from the scope and spirit of this invention will become apparent to those skilled in the art. This invention is not to be duly limited to the illustrative embodiments set forth herein.

What is claimed is:

1. A method for producing foam insulation board, the method comprising:
  forming a foam product as part of a continuous process, where said foam product includes a top planar surface, a bottom planar surface, a first longitudinally extending edge, and a second longitudinally extending edge;
  engaging each of said first edge and said second edge with a rotatable contacting element of a measuring implement to obtain first and second compressive strength measurements;
  monitoring on-line the first and second compressive strength measurements of the foam product taken along said first and second edges with said measuring implement; and adjusting said step of forming a foam product in view of data obtained from said step of monitoring.

2. The method of claim 1, further comprising the step of trimming said side edges prior to said step of monitoring.

3. The method of claim 2, where said step of trimming provides at least one trimmed edge, and where said step of monitoring includes measuring the compressive strength at the at least one trimmed edge in a direction that is perpendicular to the machine direction.

4. The method of claim 1, further comprising the step of cross-cutting the foam product into boards subsequent to said step of monitoring.

5. The method of claim 1, where said step of monitoring provides information relative to the dimensional stability of the foam product.

6. The method of claim 1, where said step of forming a foam product includes combining ingredients including reactants and a catalyst, and said step of adjusting includes altering the amount of the catalyst that is combined with the reactants.

7. The method of claim 1, where the foam product has a length, and said step of monitoring occurs along the entire length of the foam product.

8. The method of claim 1, where the foam product has a length, and said step of monitoring occurs intermittently along the length of the foam product.

9. The method of claim 1, further comprising the step of monitoring on-line the compressive strength of foam product of the continuous process along at least one side edge thereof after said step of adjusting to ensure a desired compressive strength along said at least one edge.

10. The method of claim 1, where said step of forming the foam product includes subjecting the foam product to heat prior to said step of engaging, and where said step of adjusting includes altering the heat in view of data obtained from said step of monitoring.

11. The method of claim 1, where said step of forming a foam product includes combining ingredients including reactants, catalyst, and blowing agent, and where said step of adjusting includes altering the amount of blowing agent.

12. The method of claim 1, where said step of forming a foam product includes combining an isocyanate and an isocyanate-reactive compound, and where said step of adjusting includes altering the amount of the isocyanate, the isocyanate-reactive compound, or both the isocyanate and the isocyanate-reactive compound.

13. The method of claim 1, where said step of monitoring on-line the compressive strength of the foam product provides real-time data.

14. A method of producing foam insulation board, the method comprising:
  combining ingredients including reactants and a catalyst to form a foam mixture;
  continuously forming a foam product by depositing the foam mixture on a continuously fed bottom facer and drawing the bottom facer, the foam mixture, and a continuously fed top facer through a laminator assembly to thereby form a foam product including a top planar surface defined by said top facer, a bottom planar surface defined by said bottom facer, a first longitudinally extending rise edge, and a second longitudinally extending rise edge opposite the first longitudinal rise edge, said first and second rise edges extending between said top and bottom facers;
  continuously engaging one of said first rise edge and said second rise edge between said top and bottom facers with a rotatable contacting element of a measuring implement; and
  continuously measuring on-line the compressive strength of the foam product with the measuring implement.

15. The method of claim 14, wherein said step of continuously engaging includes engaging each of said first edge and said second edge with a rotatable contacting element of a measuring implement.

16. A method of producing foam insulation product, the method comprising:
  (a) combining ingredients including reactants and a catalyst to form a foam mixture;
  (b) continuously forming a foam product by depositing the foam mixture on a continuously fed bottom facer and drawing the bottom facer, the foam mixture, and a continuously fed top facer through a laminator assembly to thereby form a foam product including a top planar surface, a bottom planar surface, a first longitudinally extending edge, and a second longitudinally extending edge opposite the first longitudinal edge;
  (c) positioning a rotatable contacting element of a measuring implement vertically between said top and bottom planar surfaces and continuously engaging one of said first edge and said second edge with the rotatable contacting element;
  (d) continuously monitoring on-line the compressive strength of the edge of the foam product with the measuring implement; and
  (e) adjusting at least one of said steps of combining ingredients and continuously forming the foam product in view of compressive strength measurements taken during said step of monitoring.

17. The method of claim 16, wherein the step of continuously forming the foam product includes continuously subjecting the foam product to increased heat following exit of the foam product from the laminator assembly and prior to the step of engaging the edges.

18. The method of claim 17, wherein the step of adjusting includes altering the heat that the foam product is subjected to.

* * * * *